United States Patent
Okamura

(10) Patent No.: US 10,286,186 B2
(45) Date of Patent: May 14, 2019

(54) GUIDING CATHETER ASSEMBLY AND METHOD OF USING THE SAME

(71) Applicant: TERUMO KABUSHIKI KAISHA, Shibuya-ku, Tokyo (JP)

(72) Inventor: Ryo Okamura, Shizuoka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 296 days.

(21) Appl. No.: 14/868,773

(22) Filed: Sep. 29, 2015

(65) Prior Publication Data

US 2016/0015940 A1  Jan. 21, 2016

Related U.S. Application Data

(63) Continuation of application No. PCT/JP2013/059942, filed on Apr. 1, 2013.

(51) Int. Cl.
| | |
|---|---|
| *A61M 25/06* | (2006.01) |
| *A61M 29/02* | (2006.01) |
| *A61M 25/00* | (2006.01) |
| *A61M 29/00* | (2006.01) |

(52) U.S. Cl.
CPC .... *A61M 25/0618* (2013.01); *A61M 25/0075* (2013.01); *A61M 25/0662* (2013.01); *A61M 29/02* (2013.01); *A61M 29/00* (2013.01)

(58) Field of Classification Search
CPC .......... A61M 25/0075; A61M 25/0618; A61M 25/0662; A61M 29/00; A61M 29/02
See application file for complete search history.

(56) References Cited

U.S. PATENT DOCUMENTS

| | | | | |
|---|---|---|---|---|
| 5,437,631 A | * | 8/1995 | Janzen | A61B 17/0057 128/898 |
| 5,599,327 A | | 2/1997 | Sugahara et al. | |
| 5,645,566 A | * | 7/1997 | Brenneman | A61B 17/0057 604/174 |
| 5,676,689 A | * | 10/1997 | Kensey | A61B 17/0057 604/168.01 |

(Continued)

FOREIGN PATENT DOCUMENTS

| | | |
|---|---|---|
| JP | 11-299897 A | 11/1999 |
| JP | 2O10-0533014 A | 10/2000 |

(Continued)

OTHER PUBLICATIONS

International Search Report (PCT/ISA/210) dated Jun. 25, 2013, by the Japanese Patent Office as the International Searching Authority for International Application No. PCT/JP2013/059942.

*Primary Examiner* — Quynh-Nhu H. Vu
(74) *Attorney, Agent, or Firm* — Buchanan Ingersoll & Rooney PC

(57) ABSTRACT

A guiding catheter assembly includes a guiding catheter which has a catheter main body and a protective sheath in covering relation to the outer peripheral portion of the catheter main body, and a dilator insertable into the guiding catheter. The protective sleeve can be moved in an axial direction with respect to the catheter main body. The protective sheath has a thin film portion which is formed of a tube-like thin film and through which the catheter main body can be inserted, and a housing portion which includes a lumen through which the catheter main body can be inserted.

7 Claims, 3 Drawing Sheets

(56) References Cited

U.S. PATENT DOCUMENTS

| | | | |
|---|---|---|---|
| 2005/0155608 A1* | 7/2005 | Pavcnik | A61B 17/0057 128/831 |
| 2007/0038245 A1* | 2/2007 | Morris | A61B 17/0057 606/213 |
| 2008/0058716 A1* | 3/2008 | Dubrul | A61B 17/3439 604/104 |
| 2012/0095448 A1 | 4/2012 | Kajii | |

FOREIGN PATENT DOCUMENTS

| | | |
|---|---|---|
| JP | 2011-072435 A | 4/2011 |
| JP | 2012-085816 A | 5/2012 |
| WO | WO 2009/007432 A1 | 1/2009 |

* cited by examiner

GUIDING CATHETER ASSEMBLY AND METHOD OF USING THE SAME

CROSS-REFERENCES TO RELATED APPLICATIONS

This application is a continuation of International Application No. PCT/JP2013/059942 filed on Apr. 1, 2013, the entire content of which is incorporated herein by reference.

TECHNICAL FIELD

The invention generally relates to a guiding catheter assembly and a method of using the same, and more particularly pertains to a guiding catheter assembly which is introduced into a lumen in a living body without using an introducer sheath.

BACKGROUND DISCUSSION

When performing, for example, therapy, examination, and the like by inserting a medical device such as a catheter or the like, into a blood vessel, in general, an introducer sheath is indwelled in a blood vessel by puncturing the skin to the blood vessel to insert the medical device into the blood vessel through the introducer sheath. However, when using such an introducer sheath, it is necessary to bore or form a large hole in the skin up to a blood vessel to accommodate a portion of the introducer sheath, and therefore, a burden on a patient increases.

In Japanese Application Publication No. 2012-85816, a catheter assembly which is designed to insert a catheter into a blood vessel without using an introducer sheath is proposed. In the catheter assembly, a dilator is inserted into the catheter which is introduced into a blood vessel in a state where the dilator protrudes from a distal portion of the catheter. The size of the puncture hole decreases as much as the portion in which the introducer sheath is not used, and therefore, it is possible to reduce a burden on a patient during puncturing.

SUMMARY

However, since no introducer sheath is used in the catheter assembly of Japanese Application Publication No. 2012-85816, the outer surface of the catheter comes into direct contact with the skin and the intravascular wall, and when the catheter is made to retreat or withdrawn, friction is caused between the skin and the intravascular wall. For this reason, there are problems in that inflammation is caused between the catheter and a biological tissue such as the skin, the inner wall of the blood vessel or the like, and in that there is large invasiveness when in use.

The invention has been made in order to solve such conventional problems, and an object of the invention is to provide a guiding catheter assembly with which it is possible to reduce a burden on a patient when moving a catheter as well as during puncturing, and a method of using the same.

According to one aspect of the disclosure here, a guiding catheter assembly includes: a guiding catheter that includes a catheter main body and a protective sheath positioned in covering relation to an outer peripheral portion of the catheter main body, with the protective sheath being axially movable with respect to the catheter main body; a dilator configured to be positioned inside the catheter main body; and wherein the protective sheath is comprised of a film portion which is formed of a tubular film and through which the catheter main body passes, and a housing portion which includes a lumen through which the catheter main body passes. With such a configuration, the protective sheath prevents friction between a biological tissue such as the skin or the like, and the catheter main body, and therefore, it is possible to reduce the burden on a patient while moving the catheter. In addition, the protective sheath is constituted so as to be supported by the catheter main body at all times, and therefore, there is little risk of causing deformation such as collapse of a thin film portion of the protective sheath, due to narrow pressure on the protective sheath caused by a biological tissue, or the like. For this reason, the portion of the protective sheath which is inserted into a lumen in a living body can be formed of a tube-like thin film.

It is preferable that the protective sheath has a valve body which is attached to the lumen of the housing portion. By doing this, it is possible to prevent leakage of blood from the space between the outer peripheral surface of the catheter main body and the inner peripheral surface of the protective sheath when inserting the catheter main body into a lumen in a living body.

Further, it is more preferable that the protective sheath has an operation mechanism which is disposed in the housing portion and is used for opening and closing the valve body. Accordingly, the protective sheath easily moves on the outer peripheral portion of the catheter main body even in a state where the valve body is installed in the protective sheath.

Further, it is preferable that a lubricant is interposed between the protective sheath and the outer peripheral portion of the catheter main body. With such a configuration, the protective sheath can more smoothly move on the outer peripheral portion of the catheter main body.

According to another aspect of the disclosure here, a method comprises: inserting a dilator into a catheter main body of a guiding catheter assembly, wherein the guiding catheter assembly includes a protective sheath at a distal portion of the catheter main body; inserting the protective sheath, together with the dilator and the catheter main body, into skin and then into a lumen in a living body; and moving the catheter main body along the lumen in the living body to position the guiding catheter at a target position by moving the dilator and the catheter main body with respect to the protective sheath.

According to the method disclosed here, the protective sheath, with which an outer peripheral portion of the catheter main body is covered and which has a thin film portion and a housing portion and can be moved in an axial direction with respect to the catheter main body, is inserted into a lumen in a living body through the skin together with the dilator and the catheter main body, and then, the dilator and the catheter main body are moved with respect to the protective sheath. Therefore, it is possible to reduce a burden on a patient even when moving the catheter as well as during puncturing.

According to another aspect, a guiding catheter assembly includes: a guiding catheter that includes a catheter main body and a protective sheath, with the catheter main body possessing an outer periphery and including a lumen extending throughout the length of the catheter main body, and wherein the lumen opens to a distal end of the catheter main body and to a proximal end of the catheter main body, and wherein the protective sheath is mounted on the catheter main body so that the protective sheath covers the outer periphery of a portion of the catheter main body. The guiding catheter assembly also includes a dilator possessing a tapered distal end, with the dilator being sized to be positioned in the lumen in the catheter main body and to be positioned relative to the catheter main body such that the tapered distal end of the dilator extends distally beyond the distal end of the catheter main body. The protective sheath is comprised of a tubular film portion and a housing portion fixed to a proximal end of the tubular film portion so that the tubular film portion and the housing portion move together, the housing portion including a valve body operable to fix the protective sheath relative to the catheter main body.

DETAILED DESCRIPTION

Figure 1:
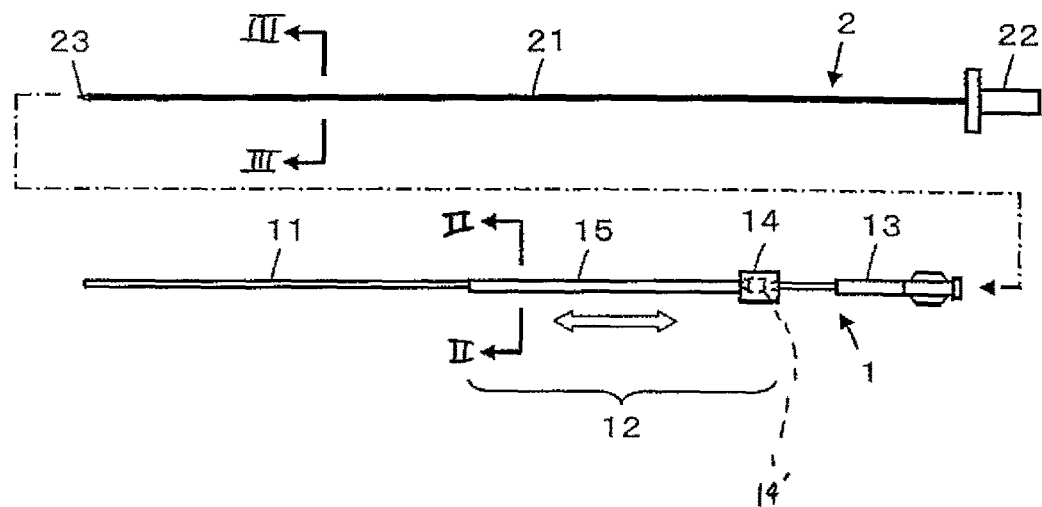
FIG. 1 is a side view showing a configuration of a guiding catheter assembly according to one embodiment disclosed here as an example of the inventive guiding catheter assembly disclosed here.

Hereinafter, an embodiment of the guiding catheter assembly representing one example of the inventive guiding catheter assembly disclosed herewill be described while referring to the accompanying drawings. Common features are identified by the same reference numerals throughout and so a detailed description of already described features will not be repeated. In some cases, dimensional ratios in the drawings are exaggerated and are different from the actual ratios for the convenience of description. In the description below, the hand operation unit side of the guiding catheter assembly will be referred to as a "proximal side" or "proximal end", and the side through which the guiding catheter assembly is inserted into the lumen in a living body will be referred to as a "distal side" or "distal end".

An overall structure of a guiding catheter assembly according to the embodiment is shown in FIG. 1. The guiding catheter assembly includes a guiding catheter 1 and a dilator 2 which is combined with the guiding catheter 1 by being inserted into the guiding catheter.

The guiding catheter 1 is formed of an elongated catheter main body 11 and a protective sheath 12 with which the outer peripheral portion of the catheter main body 11 is covered. The inside of the catheter main body 11 has a hollow tubular structure, and a hub 13 is disposed at a proximal portion of the catheter main body 11.

The protective sheath 12 has a length shorter than that of the catheter main body 11 and is formed of a tubular or tube-shaped thin film portion 15 through which the catheter main body can be inserted and a housing portion 14 which includes a lumen (generally shown in FIG. 1) through which the catheter main body can be inserted. Here, when the tube-shaped thin film is inserted into a lumen in a living body, the thin film has a thickness that allows the tubular thin film to collapse, when the tubular thin film is indwelled in a lumen in a living body, due to narrow pressure of a biological tissue such as the skin or the like, in a state where there is no member in the lumen of the tubular thin film supporting the tubular thin film (e.g., a guiding catheter or the like). For example, the thin film portion 15 is formed of a thin film with a thickness of about 0.01 mm. In addition, a distal end of the thin film portion 15 may possess a tapered shape so as to facilitate insertion into a living body. Here, the protective sheath 12 is disposed so as to be movable in an axial direction with respect to the catheter main body 11.

In addition, a valve body (schematically in FIG. 1 and identified as 14') is liquid-tightly attached to the inside of the housing portion 14 of the protective sheath 12. Here, the valve body 14' is preferably an elastic valve body 14' which is made of a material such as silicon or the like. The housing portion 14 preferably has an operation mechanism for opening and closing the valve body 14'. The operation mechanism can selectively change the state of the protective sheath 12 between an open state, in which the protective sheath 12 is allowed to move with respect to the catheter main body 11 by opening a gap between the outer peripheral surface of the catheter main body 11 and the protective sheath, and a closed state in which the position of the protective sheath 12 relative to the catheter main body 11 is fixed by closing the gap between the outer peripheral surface of the catheter main body 11 and the protective sheath and regulating the movement of the protective sheath 12 with respect to the catheter main body 11. For example, the housing portion 14 has a cap structure at a proximal end, and the valve body 14' can be compressed by rotating or pushing the cap structure to operate the opening/closing of the valve body 14'. The illustration of the housing portion 14 is thus a schematic illustration of the operation mechanism.

In contrast, the dilator 2 includes a dilator main body 21 having a length substantially the same as the total length of the catheter main body 11, and a grip portion 22 is disposed at a proximal portion of the dilator main body 21.

Figure 2:
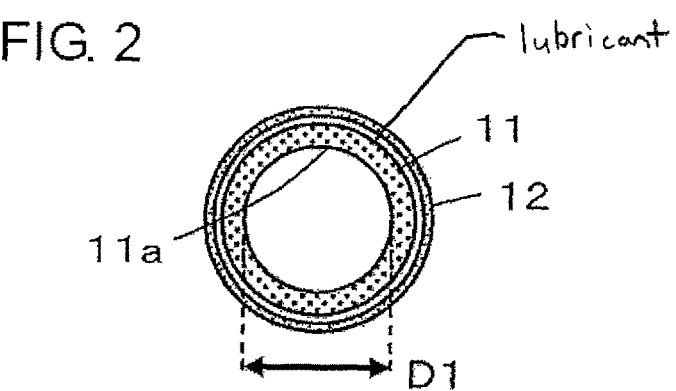
FIG. 2 is a cross-sectional view taken along the section line II-II of FIG. 1.
Figure 3:
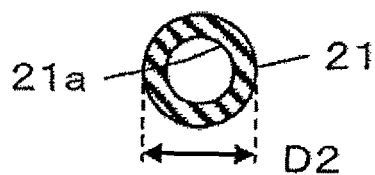
FIG. 3 is a cross-sectional view taken along the section line III_III of FIG. 1.

As shown in FIG. 2, the catheter main body 11 has a lumen 11a having an internal diameter D1 sized for inserting the dilator main body 21, a medical catheter, and the like into the lumen 11a. As shown in FIG. 3, the dilator main body 21 has an outer diameter D2 smaller than the internal diameter D1 of the lumen 11a of the catheter main body 11, and a lumen 21a for inserting a guide wire into the lumen 21a of the dilator main body 21.

The material forming the catheter main body 11 preferably has flexibility to some degree and examples thereof include polyolefins such as polyethylene, polypropylene, ethylene-propylene copolymers, ethylene-vinyl acetate copolymers or the like; and resin materials such as polyvinyl chloride, polyurethane, polyamide, polyamide elastomer, polyimide, silicon resin, polyether ether ketones, polyester, polyester elastomer or the like.

Examples of the material forming the protective sheath 12 include general-purpose resins such as polyethylene, polypropylene, polyurethane, polyamide, polyether block amide copolymers or the like; fluoro-based resins such as FEP (tetrafluoroethylene/hexafluoropropylene copolymer), PFA (perfluoroethylene/perfluoroalkyl vinyl ether copolymer), ETFE (ethylene/tetrafluoroethylene copolymer), PTFE (polytetrafluoroethylene), PVDF (polyvinylidene fluoride), THV (thermoplastic resins formed of three kinds of monomers of tetrafluoroethylene, hexafluoropropylene, and vinylidene fluoride) or the like; super engineering plastics such as PEK (polyether ketone), PEEK (polyether ether ketone), PPS (polyphenylene sulfide), PI (thermoplastic polyimide), PSF (polysulfone), PEI (polyetherimide), PES (polyethersulfone) or the like; and metallic materials.

The dilator main body 21 can be formed of the same materials as that of the above-described catheter main body 11 and the protective sheath 12.

Figure 4:
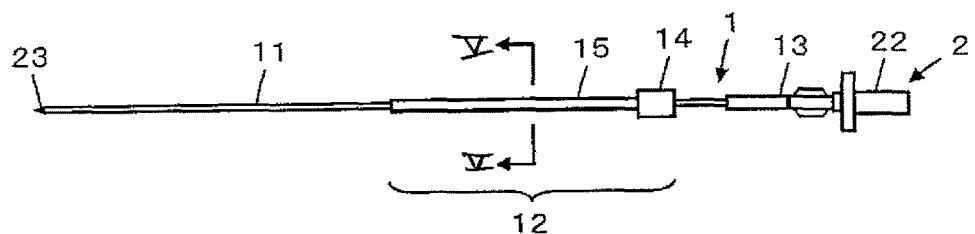
FIG. 4 is a side view showing a state in which a dilator is combined with a catheter main body by being inserted into the catheter main body.
Figure 5:
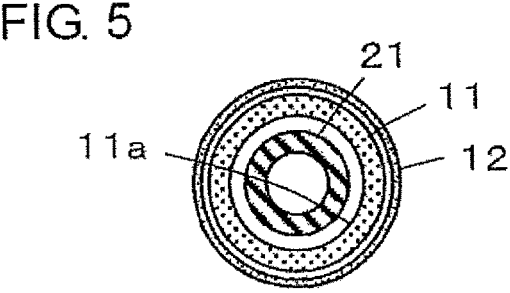
FIG. 5 is a cross-sectional view taken along the section line V-V of FIG. 4.

It is possible to combine the guiding catheter 1 and the dilator 2 by inserting the dilator main body 21 into the lumen 11a of the catheter main body 11 through the hub 13 of the guiding catheter 1 until a distal portion 23 of the dilator main body 21 protrudes forward from or distally beyond a distal end of the catheter main body 11 as shown in FIG. 4. As illustrated in FIG. 1, the distal portion 23 of the dilator main body 21 terminated at a tapered distal end. At this time, as shown in FIG. 5, the catheter main body 11 is disposed inside the protective sheath 12 and the dilator main body 21 is disposed inside the lumen 11a of the catheter main body 11.

The hub 13 of the guiding catheter 1 and the grip portion 22 of the dilator 2 each have an engagement structure configured to interlock the hub 13 and the grip portion 22 with each other in a state where the dilator 2 is combined with the guiding catheter 1 as shown in FIG. 4. For example, the engagement structure may be configured so that the dilator 2 and the guiding catheter 1 are integrally engaged with each other simply through an operation of pushing the dilator 2 into the hub 13 of the guiding catheter 1. This can be accomplished by configuring the engagement structure such that an engagement groove is provided in the hub 13 of the guiding catheter 1 and a locking claw for engaging the engagement groove of the hub 13 is provided on the grip portion 22 of the dilator 2.

Next, a method of using the guiding catheter assembly according to Embodiment 1 will be described.

First, the dilator 2 is combined with the guiding catheter 1 to interlock the hub 13 and the grip portion 22 with each other as shown in FIG. 4, and the valve body 14' of the housing portion 14 of the protective sheath 12 is positioned in the open state. At this time, the distal portion of the catheter main body 11 extends in a linear shape (straight shape) and the distal portion 23 (tapered distal portion) of the dilator main body 21 protrudes forward from or distally beyond the distal end of the catheter main body 11, through insertion of the dilator main body 21 into the lumen 11a of the catheter main body 11. According to this example, at the time the dilator 2 is combined with the guiding catheter 1 (i.e., when the dilator 2 is inserted into the guiding catheter 1), the protective sheath 12 is mounted on the catheter main body 11.

Figure 6:
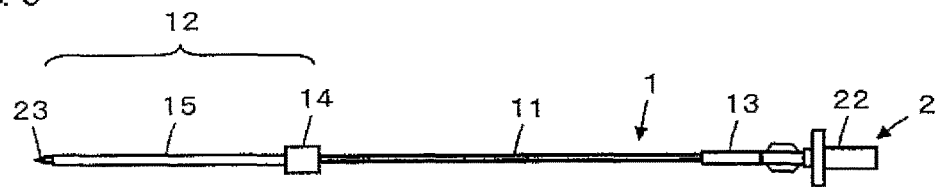
FIG. 6 is a side view showing a state in which a protective sheath is moved to a distal portion of a catheter main body.

From this state, the protective sheath 12 is moved in a distal direction along the catheter main body 11 and is positioned in the vicinity of the distal portion of the catheter main body 11 as shown in FIG. 6. The protective sleeve 12 is moved forwardly in the distal direction to a position in which the distal portion 23 of the dilator main body 21 protrudes forward from or distally beyond the distal portion of the catheter main body 11 and also protrudes forward from or distally beyond the distal portion of the protective sheath 12. Here, the valve body 14' of the housing portion 14 of the protective sheath 12 is set to a closed state (i.e., the valve body is operated to shift the valve body to a closed state) to fix a relative position of the protective sheath 12 with respect to the catheter main body 11. The valve body 14' is changed to the closed position after moving the protective sheath 12 in the forward direction to the desired position such as shown in FIG. 6. It is preferable to grip the housing portion 14 of the protective sheath 12 when moving the protective sheath 12 (i.e., it is preferable to axially move the protective sleeve 12 by gripping and axially moving the housing portion 14). In this manner, it is possible to move the protective sheath 12 without touching the thin film portion 15 which enters a lumen in a living body.

Figure 7:
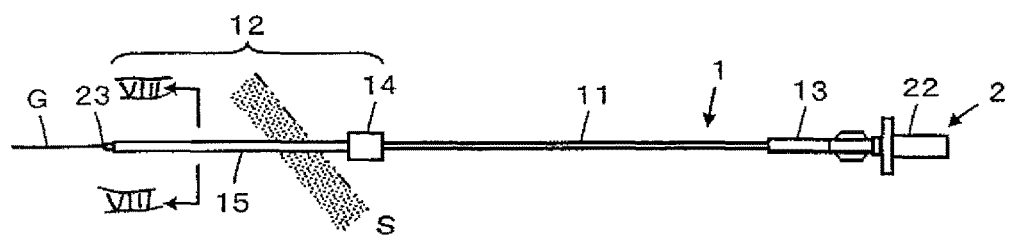
FIG. 7 is a side view showing a state in which the guiding catheter assembly is inserted into a blood vessel through the skin.
Figure 8:
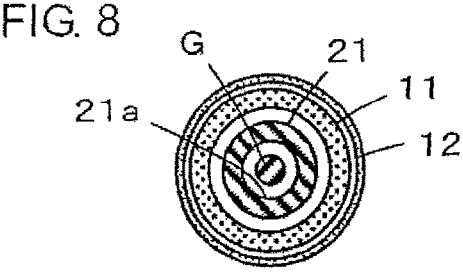
FIG. 8 is a cross-sectional view taken along the section line VIII-VIII of FIG. 7.

Next, as shown in FIG. 7, the guiding catheter assembly (the guiding catheter 1 and the dilator 2) is inserted into a blood vessel of a patient through the patient's skin skin S by moving the guiding catheter assembly along a guide wire G which is previously secured in the blood vessel in advance through the Seldinger technique or the like. At this time, as shown in FIG. 8, the guide wire G is inserted into or positioned in the lumen 21a of the dilator main body 21.

Figure 9:
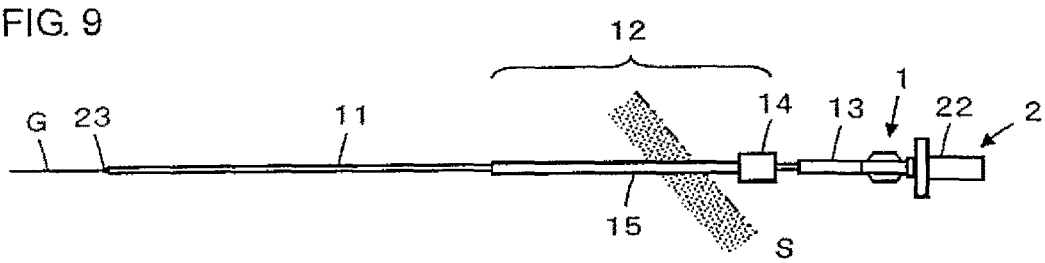
FIG. 9 is a side view showing a state in which the catheter main body and the dilator are advanced with respect to the protective sheath.

The state of the valve body 14' of the housing portion 14 of the protective sheath 12 is returned to an open state as shown in FIG. 9 when the thin film portion 15 of the protective sheath 12 is inserted into the blood vessel, and the hub 13 of the catheter main body 11 and the grip portion 22 of the dilator 2 are moved relative to the protective sheath 12. That is, after the guiding catheter assembly is introduced into a blood vessel as shown in FIG. 7, with the protective sleeve 12 in the blood vessel, the valve body 14' of the housing portion 14 of the protective sheath 12 is returned to an open state, and the hub 13 of the catheter main body 11 and the grip portion 22 of the dilator 2 are both moved in the forward or distal direction relative to the protective sheath 12 as shown in FIG. 9. Accordingly, the catheter main body 11 and the dilator main body 21 are advanced relative to the protective sheath 12. Accordingly, the catheter main body 11 and the dilator main body 21 advance into the blood vessel while the thin film portion 15 of the protective sheath 12 remains indwelled at a position at which the thin film portion is inserted into or positioned in the blood vessel through the skin S. At this time, the skin S and the inner wall of the blood vessel are protected by the protective sheath 12, and therefore, are not damaged even if the catheter main body 11 and the dilator main body 21 are moved.

Figure 10:
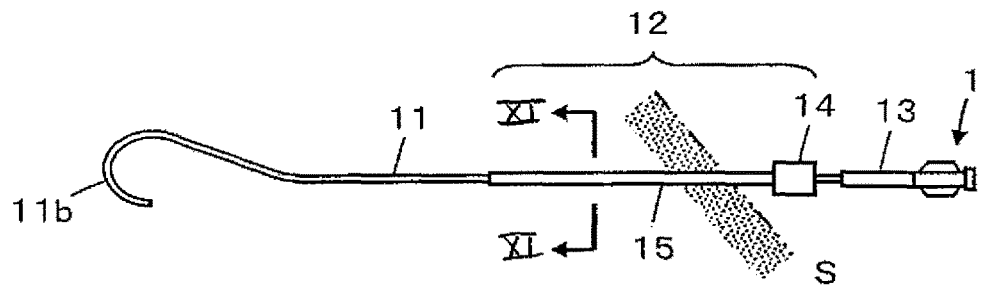
FIG. 10 is a side view showing a state in which the distal portion of the catheter main body is engaged with the vicinity of a target position in a blood vessel.

Then, when the distal portion of the catheter main body 11 reaches a target position, for example, a coronary artery entrance, the dilator main body 21 is removed from the lumen 11a of the catheter main body 11 as shown in FIG. 10 and the distal portion 11b of the catheter main body 11 is locked in the vicinity of the target position. Then, the valve body 14' of the housing portion 14 of the protective sheath 12 is operated so that the valve body 14' is shifted to the closed state. Accordingly, the relative position of the catheter main body 11 with respect to the protective sheath 12 is fixed and the gap between the inner peripheral surface of the housing portion 14 and the outer peripheral surface of the catheter main body 11 is closed, thereby preventing the leakage of blood from the blood vessel.

Figure 11:
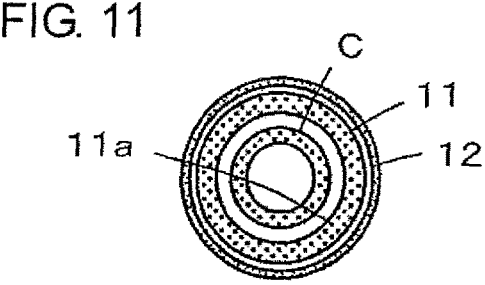
FIG. 11 is a cross-sectional view corresponding to the section line XI-XI of FIG. 10 when a therapeutic catheter is inserted into the catheter main body.

In this manner, it is possible to perform therapy of a target site by inserting a therapeutic catheter C or the like, which is required for therapy, into the lumen 11a of the catheter main body 11 from the hub 13 as shown in FIG. 11 in a state where the catheter main body 11 is locked.

Advantages associated with the guiding catheter assembly disclosed here will be further described in detail below using an example, but the present invention is not limited to this example.

EXAMPLE (Production of Thin Film Portions of Protective Sheaths)

Fluororesin (ETFE copolymer) was extruded on an outer peripheral surface of a columnar core material in a tubular shape through hollow extrusion molding to produce a thin film portion of a protective sheath possessing an inner diameter of 2.22 mm×an outer diameter of 2.36 mm (thickness of 0.07 mm). In addition, a thin film portion of a protective sheath possessing an inner diameter of 2.22 mm and an outer diameter of 2.62 mm (wall thickness of 0.20 mm) was produced in the same procedure.

(Confirmation of Rigidity of Thin Film Portion)

Guiding catheters were passed through lumens of the thin film portion with a thickness of 0.07 mm and the thin film portion with a thickness of 0.20 mm which were produced as described above, and the guiding catheters on which the thin film portions were disposed were inserted into silicon skin models (TRI puncture model of Y0229-99T2-330, Kyoto Kagaku, Co., Ltd.). Then, the guiding catheter was moved forward and backward about 10 times in a state where parts of the thin film portions which were disposed on the guiding catheters were inserted into the skin models, and the guiding catheters were finally removed from the lumens of the thin film portions. In addition, the same experiment as that described above was performed using a guiding catheter on which no thin film portion was disposed.

As a result, in the guiding catheters on which the thin film portions were disposed, and the guiding catheter on which no thin film portion was disposed, it was possible to confirm that damage on a puncture hole of the skin model due to the guiding catheter was large in the guiding catheter on which no thin film portion was disposed. In addition, it was impossible to visually confirm any difference in damage on the skin models in the two guiding catheters on which the thin film portions were disposed. For this reason, the thickness of a thin film portion is preferably relatively thin from the viewpoint of reducing a burden on a patient, and therefore, the thin film portion which is formed of fluororesin (ETFE copolymer) and has a thickness of 0.07 mm is most preferable. In addition, after removing the guiding catheters, it was possible to maintain (no collapse) the shape of the tube portion of the thin film portion with a thickness of 0.20 mm which was inserted into the skin model, even with the elasticity of the skin model, whereas it was impossible to maintain (collapse) the shape of the tube portion of the thin film portion with a thickness of 0.07 mm which was inserted into the skin model, due to elasticity of the skin model. Thus, the thin film portion possessing the larger thickness was able to maintain the tubular shape of the thin film portion in spite of the elasticity force applied by the skin model upon removal of the guiding catheter and was thus able to avoid collapse, whereas the thin film portion possessing the smaller thickness was not as well suited to avoiding collapse under the elasticity force of the skin model upon removal of the guiding catheter and was thus not as easily able to maintain the tubular shape of the thin film portion. However, when inserting a guiding catheter into a lumen in a living body during actual use, a thin film portion is supported by the guiding catheter at all times. Therefore, there is no problem even with a thickness of the thin film portion with which it is impossible to maintain the shape of the thin film portion under narrow pressure of a biological tissue such as the skin or the like.

In addition, in an introducer sheath of an introducer assembly, the size of a puncture hole becomes larger as the outer periphery of the cross section of the introducer sheath becomes larger, and therefore, a burden on a patient is increased. For this reason, the thickness of the introducer sheath should preferably be thin from the viewpoint of reducing the burden on a patient. However, as can be seen from the aforesaid results, when the thickness of the introducer sheath formed of fluororesin (ETFE copolymer) is about one third of that of the current introducer sheath (thickness of 0.20 mm), for example, to less than or equal to 0.07 mm, it is impossible to maintain the shape of the tube portion when the narrowing pressure of a biological tissue such as the skin or the like is applied. For this reason, in a usual method of using an introducer sheath, that is, in a method of indwelling the introducer sheath, into which a dilator is inserted, in a lumen in a living body and removing the dilator from the introducer sheath, and then, inserting a guiding catheter into the introducer sheath which has been indwelled in the lumen in a living body, it is impossible to maintain the shape of the introducer sheath with respect to the portion which has been indwelled in the lumen in a living body if the thickness of the introducer sheath formed of fluororesin (ETFE copolymer) is less than or equal to 0.07 mm. Therefore, it is impossible to insert the guiding catheter into the introducer sheath and to exhibit a usual function as an introducer sheath. Therefore, the thin film portion of the present application is effective from the viewpoint of reducing a burden on a patient since the thin film portion of the present application has the same function as that of the introducer sheath and it is possible to make the thickness of the introducer sheath thinner than that of the existing introducer sheath.

Here, in order to reduce the size of the puncture hole, the tube-like thin film portion has a thickness which does not allow maintenance of the shape of the tube portion, which has been indwelled in a lumen in a living body, due to an applied narrowing pressure of the skin or the like in a state where there is no support member such as a guiding catheter or the like in the lumen of the tube. Specifically, the thickness of the thin film portion is preferably less than or equal to 0.07 mm. The thickness of the thin film portion is preferably greater than or equal to 0.01 mm in order to prevent buckling or the like from being caused when inserting the thin film portion into a lumen in a living body.

As described above, the protective sheath 12 is used in a state where the protective sheath 12 covers the outer peripheral surface of the catheter main body 11 at all times. There is no case where only the protective sheath 12 is indwelled in a blood vessel from the skin S, for example in a state where the catheter main body 11 is removed from the protective sheath 12. For this reason, rigidity as in the case of a conventional introducer sheath is not required, and it is possible to form the thin film portion to be extremely thin. As a result, the size of a puncture hole when a guiding catheter is inserted into a lumen in a living body using the protective sheath 12 of the present application is smaller than the size of a puncture hole when a guiding catheter is inserted into a lumen in a living body using a conventional introducer sheath. For this reason, it is possible to reduce a burden on the patient during puncturing, when using the protective sheath 12 disclosed here. In addition, after inserting the protective sheath 12 into a blood vessel through the skin S together with the catheter main body 11 and the dilator main body 21, the catheter main body 11 and the dilator main body 21 are relatively moved with respect to the protective sheath 12. Therefore, the skin S and the inner wall of the blood vessel are protected by the protective sheath 12 and the burden on the patient is reduced even during movement of the catheter main body 11 and the dilator main body 21.

It is desirable that a lubricant such as silicon, a hydrophilic polymer or the like, is interposed between the protective sheath 12 and the outer peripheral surface of the catheter main body 11 in order to facilitate relative movement between the protective sheath 12 and the catheter main body 11.

In addition, if the outer peripheral surface of the catheter main body 11, the outer peripheral surface of the dilator main body 21, and the outer peripheral surface of the protective sheath 12 are coated with a hydrophilic polymer, nitro oxide, heparin, or the like, it is possible to achieve a reduction in the incidence rate of spasm (coronary spastic angina) and a reduction in removal resistance during spasm, which is preferable.

In the embodiment described above, the guiding catheter assembly is inserted into a blood vessel. However, the invention is not limited in this way and it is possible to apply the guiding catheter assembly of the present invention to a lumen in a living body, such as bile ducts, trachea, esophagus, urethra or the like.

The detailed description above describes an embodiments of a guiding catheter assembly and method representing examples of the inventive guiding catheter assembly and method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A method comprising: inserting a dilator into a catheter main body of a guiding catheter assembly, the guiding catheter assembly including a protective sheath at a distal portion of the catheter main body; inserting the protective sheath, together with the dilator and the catheter main body, into skin and then into a lumen in a living body; and moving the catheter main body in a forward direction along the lumen in the living body to position the guiding catheter at a target position by moving the dilator and the catheter main body in the forward direction with respect to the protective sheath.

2. The method according to claim 1, further comprising: before inserting the protective sheath, together with the dilator and the catheter main body, into skin and then into a lumen in a living body, moving the protective sheath relative to the catheter main body in a distal direction toward a distal end of the catheter main body to position the protective sheath in a vicinity of the distal end of the catheter main body.

3. The method according to claim 2, wherein the protective sheath is in a fixed position relative to the catheter main body before moving the protective sheath relative to the catheter main body in the distal direction, further comprising releasing the fixed position of the protective sheath relative to the catheter main body before moving the protective sheath relative to the catheter main body in the distal direction.

4. The method according to claim 3, further comprising: fixing the position of the protective sheath relative to the catheter main body after the protective sheath is moved to the vicinity of the distal end of the catheter main body.

5. The method according to claim 1, further comprising: fixing the protective sheath relative to the catheter main body after the moving of the dilator and the catheter main body in the forward direction with respect to the protective sheath.

6. The method according to claim 1, further comprising: removing the dilator from the catheter main body.

7. The method according to claim 6, further comprising: fixing the protective sheath in position relative to the catheter main body after removing the dilator from the catheter main body.

\* \* \* \* \*